United States Patent [19]

Beard

[11] Patent Number: 5,003,095

[45] Date of Patent: Mar. 26, 1991

[54] PROCESS FOR PREPARING METHYLALUMINOXANES

[75] Inventor: William R. Beard, Baton Rouge, La.

[73] Assignee: Ethyl Corporation, Richmond, Va.

[21] Appl. No.: 490,313

[22] Filed: Mar. 8, 1990

[51] Int. Cl.$^5$ .................................................. C07F 5/06
[52] U.S. Cl. ...................................................... 556/179
[58] Field of Search ................................. 556/179, 178

[56] References Cited

U.S. PATENT DOCUMENTS

| | | | |
|---|---|---|---|
| 3,242,099 | 3/1966 | Manyik et al. ..................... | 252/429 |
| 4,364,872 | 12/1982 | Diefenbach ........................ | 260/448 |
| 4,544,762 | 10/1985 | Kaminsky et al. ................. | 556/179 |
| 4,665,208 | 5/1987 | Welborn, Jr. et al. ............ | 556/179 |
| 4,730,072 | 3/1988 | Schoenthal et al. ............... | 556/179 |
| 4,772,736 | 9/1988 | Edwards et al. ................... | 556/179 |
| 4,908,463 | 3/1990 | Bottelberghe ..................... | 506/179 |

*Primary Examiner*—Arthur C. Prescott
*Attorney, Agent, or Firm*—David M. Bunnell

[57] ABSTRACT

Alkylaluminoxanes having 2 or more carbons in the alkyl group are reacted with a methyl halide using a bismuth containing catalysts to form methylaluminoxane by alkyl group exchange.

8 Claims, No Drawings

PROCESS FOR PREPARING METHYLALUMINOXANES

BACKGROUND

This invention relates generally to a process for making methylaluminoxanes and more specifically to the preparation of methylaluminoxanes from higher alkylaluminoxanes by a catalyzed, alkyl-group-exchange reaction.

Hydrocarbylaluminoxanes, including methylaluminoxanes complexed with transition metal compounds, have been found to be very effective olefin polymerization catalysts (Manzik et al. U.S. Pat. No. 3,242,099). Hydrocarbylaluminoxanes can be made by the controlled partial hydrolysis of hydrocarbyl aluminum compounds and methylaluminoxanes have been prepared in this manner. However, this requires the preparation and purification of trimethylaluminum. Higher alkylaluminoxanes and especially ethylaluminoxanes are easier to prepare on a commercial scale. I have found that methylaluminoxanes can be prepared by reacting a higher alkylaluminoxane with a methylhalide so as to exchange the methyl group for the higher alkyl group. Such exchanges have been used to prepare trimethylaluminum from triethylaluminum as disclosed in U.S. Pat. No. 4,364,872 using a bismuth based catalyst; but the effect of using such catalysts with aluminoxanes, which are complex compounds containing the

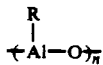

unit, where R is an alkyl group and n is about 1-20, and which can be linear or cyclic compounds, could not be predicted.

SUMMARY

In accordance with this invention, there is provided a process for making methylaluminoxanes comprising reacting an alkylaluminoxane, having at least two carbon atoms in the alkyl group, with methyl halide in the presence of a bismuth-based catalyst so as to exchange methyl groups for the alkyl groups in the trialkylaluminoxane and recovering a methylaluminoxane.

DETAILED DESCRIPTION

Alkylaluminoxanes may exist in the form of linear or cyclic polymers with the simplest compounds being a tetraalkylaluminoxane such as tetramethylaluminoxane, $(CH_3)_2AlOAl(CH_3)_2$, or tetraethylaluminoxane, $(C_2H_5)_2AlOAl(C_2H_5)_2$. The compounds preferred for use in olefin polymerization catalysts usually contain about 9 to 20 of the repeating units:

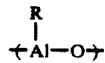

where R is $C_1$-$C_8$ alkyl.

The alkylaluminoxane starting compounds used in the alkyl exchange process of the invention can be made as is known in the art by partial hydrolysis of the corresponding trialkylaluminum compounds.

Ethylaluminoxane is the preferred compound for use in the process but other compounds having alkyl groups of 2 or more carbon atoms, preferably up to about 8 carbons and most preferably 2-4 carbons, can be used, for example, propylaluminoxane, isobutylaluminoxane, n-butylaluminoxane, n-hexylaluminoxane, n-octylaluminoxane and the like.

The alkylaluminoxanes are solids which are conveniently added to the reaction as slurries in an inert hydrocarbon solvent such as a liquid alkane, e.g. pentane, hexane, heptane, octane, or decane. Aromatic solvents such as benzene and alkyl benzenes such as cyclohexane, toluene, ethyl benzene, or xylene can be used but are less preferred because of the possibility of aromatic ring alkylation occurring during the alkyl exchange reaction.

The methyl halide can be methylchloride, methyl bromide or methyl iodide. The methyl halide is usually used in excess of the amounts of alkyl groups to be exchanged and can be used in from about 1 to 10 moles or more per equivalent weight of alkylaluminoxane, where one equivalent weight is the molecular weight of the repeat unit:

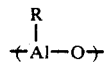

At least a slight excess of methyl halide is needed to provide for the replacement of alkyl groups.

The bismuth-based catalysts that may be used in the invention include alkyl or aryl bismuth compounds, inorganic bismuth salts, and bismuth metal. Any bismuth compound may be used which is capable of forming an alkyl bismuth bond or an aryl bismuth bond. Triphenyl bismuth $[Bi(C_6H_5)_3]$, bismuth (III) chloride $(BiCl_3)$, and trimethyl bismuth $(BiMe_3)$, are the preferred bismuth compounds for use as as a catalyst component. Specific examples of other suitable catalyst components include bismuth halides such as bismuth (III) bromide $(BiBr_3)$ and bismuth (III) iodide $(BiI_3)$ and alkyl bismuths such as triethyl bismuth.

The preferred catalyst is prepared by reacting a slurry of bismuth chloride in a hydrocarbon solvent with approximately an equimolar quantity of a trialkylaluminum and most preferably triethylaluminum. The catalyst complex may also be formed with trimethylaluminum or even the alkylaluminoxane reactant.

The catalyst can be formed in situ by adding the components to the reaction mixture or by premixing the components in a hydrocarbon solvent and adding the preformed catalyst mixture to the reaction. Catalyst which has been formed in a prior alkyl exchange process can be recycled.

The amount of bismuth-based catalyst employed is susceptible to variation. Amounts of as little as one half to two mole percent and as high as 50 mole percent, based on the equivalent weight of alkylaluminoxane, are effective. The amount should be sufficient to provide the desired reaction rate.

It is convenient to use a solvent in the process of the invention although such use is optional. The preferred solvents are aliphatic hydrocarbons, both cyclic and acyclic e.g. pentane, hexane, heptane, octane, cyclohexane, and decane. Aromatic hydrocarbons may also be used provided they do not alkylate under reaction conditions.

Ordinarily, reaction temperatures will fall in the range of about 50° C. to about 150° C. Some variation from this range may be permissible. A temperature of about 100°–125° C. provides a convenient reaction rate. In general, temperature and catalyst concentration can be varied to achieve the desired reaction rate so as to complete the reaction in about 1 to 4 hours.

The catalytic alkyl group exchange reaction can be conducted by charging a reactor with the reactants, solvent, and catalyst in an inert atmosphere, sealing the reactor, and then heating the reactor with stirring of the reaction mixture at the desired temperature of 100°–125° C. for 1–2 hours. The most volatile materials are then removed by vacuum distillation and condensed in a cold trap to leave the product as a nonvolatile residue.

The invention is further illustrated by, but is not intended to be limited to, the following examples in which parts and percentages are by weight unless otherwise indicated.

EXAMPLE 1

The reactor was a three-ounce Fisher-Porter tube with a 500-psi rating which was fitted with a relief valve set for 350 psi, a 0–300 psig stainless steel pressure gauge, a thermocouple well which extended to within two cm of the bottom, and a stainless steel bellows valve. It was equipped with a magnetic stirring bar, a coupling insert, and an "O"-ring seal.

The reactor had previously been used for a 140° C./15 min. transalkylation reaction using triethylaluminum (TEA), MeBr, and $BiBr_3$ in decane solvent. All of the volatile reaction products, including the decane, had been distilled from the reactor on the vacuum line, leaving the nonvolatile catalyst residue in the reactor. In an inert atmosphere glove box, the reactor was further charged with 16.8 grams of EAO(ethylaluminoxane)/heptane slurry (approximately 26 mmols of EAO repeat unit), followed by 16.5 grams of decane. The reactor was sealed, removed from the glove box, and then 23.4 grams (246 mmols) of MeBr were added to it on the vacuum line.

The reactor was resealed and then heated in an oil bath at 121°–123° C. for 2 hours after which the most volatile materials were distilled on the vacuum line and condensed in a −196° C. detachable U-trap. The distillate, as analyzed by $^1H$ NMR and wet chemistry, was found to contain ethyl bromide, methyl bromide, alkanes, and some aluminum values. The less volatile material, a thin white slurry, was also analyzed by $^1H$ NMR and wet chemistry. It consisted of heptane, decane, Al-Me, and Al-Et groups along with some hydrolyzable bromine, presumably present as Al-Br groups. The gas analysis gave EtH 14% and MeH 84%. The Br/Al ratio was 0.30, the gas/Al ratio was 1.09, and the (gas+Br)/Al ratio was 1.38. The results indicate that 84% of the ethyl groups in the EAO had been replaced by methyl groups.

EXAMPLE 2

In an inert atmosphere glove box, a 10-mmOD Pyrex tube, which was sealed to a 4-mm Chemglass high vacuum stopcock, was charged with a catalytic amount estimated to be about 50 mgs of $BiCl_3$ followed by 0.26 gram of EAO/heptane slurry (approximately 0.4 mmol of EAO repeat unit), 1.12 grams of decane, and 0.26 gram (2.3 mmols) of triethylaluminum. The tube was sealed and removed from the glove box after which 12 mmols of MeBr were condensed into it on the vacuum line. The Pyrex tube was sealed-off, placed inside of a half-inch stainless steel tube, one end of which was plugged while the other end was vented to the back of the hood, and then heated in a 100°–120° C. oil bath for one hour. The $^1H$ NMR spectrum of the product mixture had resonances typical of alkanes, ethyl bromide and methyl bromide in addition to two resonances (one major, one minor) typical of Me-Al groups. No resonances typical of Et-Al groups were present. The solvents and volatile reaction products were stripped on the vacuum line, leaving a nonvolatile residue. Its $^1H$ NMR spectrum had several resonances typical of Me-Al groups, minor quartets@2.4–2.8 ppm, which are characteristic of the transalkylation catalyst, as well as other unassigned resonances including a major singlet at 1.55 ppm. Again, no resonances characteristic of Al-Et groups were present indicating that substantially complete conversion of the starting ethylaluminoxane to methylaluminoxane was accomplished.

What is claimed is:

1. A process for making methylaluminoxane comprising reacting alkylaluminoxane, having at least two carbon atoms in the alkyl group, with methyl halide in the presence of a bismuth-based catalyst so as to exchange methyl groups for the alkyl groups in the alkylaluminoxane and recovering methylaluminoxane.

2. A process for making methylaluminoxane comprising reacting a mixture, said mixture comprising (a) an alkylaluminoxane having at least two carbon atoms in the alkyl group (b) from about 1 to 10 moles per equivalent of said alkylaluminoxane of a methyl halide, (c) an inert hydrocarbon solvent, and (d) from about 0.005 to 0.5 mole of a bismuth-based catalyst per equivalent of said alkylaluminoxane, at a temperature of from about 50° to 150° C. for from about 1 to 4 hours, said catalyst being formed from bismuth, or a bismuth compound, and a trialkylaluminum, and recovering methylaluminoxane.

3. The process according to claim 2 wherein said alkylaluminoxane is ethylaluminoxane, said methyl halide is methyl bromide and said bismuth-based catalyst is formed from triethylaluminum and a bismuth trihalide or bismuth triphenyl.

4. The process according to claim 3 wherein said methyl halide is methyl bromide and said bismuth-based catalyst is formed from a bismuth trihalide.

5. The process according to claim 4 wherein said bismuth trihalide is bismuth trichloride.

6. The process according to claim 2 wherein said bismuth-based catalyst is formed in-situ by adding bismuth or a bismuth containing compound and a trialkylaluminum to the reaction mixture.

7. The process according to claim 2 wherein said bismuth-based catalyst is preformed and added to the reaction mixture.

8. The process according to claim 5 wherein the solvent is decane, the reaction temperature is from about 100° to 125° C. and the reaction time is from about 1 to 2 hours.

* * * * *